(12) United States Patent
Ollivier et al.

(10) Patent No.: US 7,483,753 B2
(45) Date of Patent: Jan. 27, 2009

(54) CORONARY PROBE INCLUDING A SOPHISTICATED RETENTION STRUCTURE

(75) Inventors: Jean-Francois Ollivier, Villiers le Bacle (FR); Jean-Michel Tacou, Conches sur Gondoire (FR)

(73) Assignee: ELA Medical S.A.S., Montrouge (FR)

( * ) Notice: Subject to any disclaimer, the term of this patent is extended or adjusted under 35 U.S.C. 154(b) by 310 days.

(21) Appl. No.: 10/607,197

(22) Filed: Jun. 25, 2003

(65) Prior Publication Data

US 2004/0059401 A1 Mar. 25, 2004

(30) Foreign Application Priority Data

Jun. 26, 2002 (FR) .................................. 02 07909

(51) Int. Cl.
*A61N 1/375* (2006.01)
(52) U.S. Cl. ..................................... 607/126
(58) Field of Classification Search ............... 607/126, 607/127, 122, 130, 131; 600/381, 374, 375
See application file for complete search history.

(56) References Cited

U.S. PATENT DOCUMENTS 4,550,737 A * 11/1985 Osypka ...................... 607/127
6,006,122 A 12/1999 Smits .......................... 600/373
6,136,021 A 10/2000 Tockman et al. ............. 607/122
6,385,492 B1 * 5/2002 Ollivier et al. ............... 607/122
6,556,874 B2 * 4/2003 Audoglio ..................... 607/126
6,944,507 B2 * 9/2005 Froberg et al. .............. 607/126

* cited by examiner

*Primary Examiner*—Mark W Bockelman
*Assistant Examiner*—Eric D Bertram
(74) *Attorney, Agent, or Firm*—Orrick Herrington & Sutcliffe, LLP

(57) ABSTRACT

A coronary probe for stimulation of the heart having a sophisticated retention structure. The probe is intended to be implanted in a vein of the coronary network for the stimulation of a left cavity of the heart by an active implantable medical device. It includes a flexible hollow sheath (10) including an internal conductor, an intermediate element (12) with a cylindrical body (24) bearing retention structure, and an end forming a probe-head (14) that is equipped with at least one stimulation electrode (20). The retention structure includes at least one relief (28) formed on the cylindrical body (24) and presenting, as seen from the end, an overall circular contour so as to have locally an increased diameter compared to the diameter of the cylindrical body. This contour is eccentric compared to the axis (D) of cylindrical body. The relief is more preferably a helicoid relief with a thread (30) extending around the cylindrical body, in particular a nonjointed thread, with a variable nominal radius growing then decreasing, and with constant step and of a round profile.

8 Claims, 1 Drawing Sheet

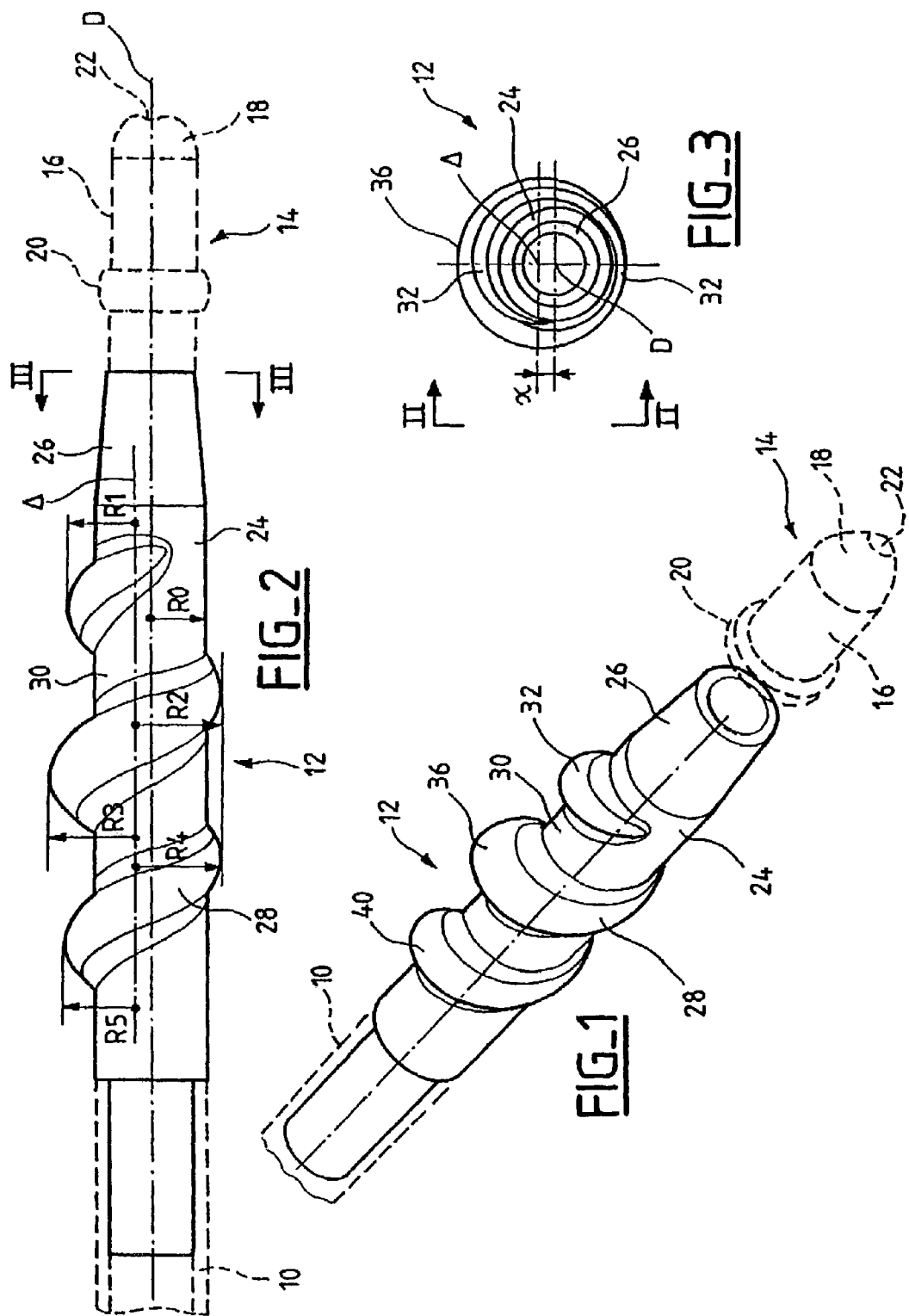

CORONARY PROBE INCLUDING A SOPHISTICATED RETENTION STRUCTURE

FIELD OF THE INVENTION

The present invention relates to probes for cardiac stimulation that are intended to be implanted in the coronary network of the heart to allow for the stimulation of a left heart cavity. The present invention more particularly concerns the structure for retaining a probe, making it possible to ensure the maintenance of the extremity of the probe in the chosen site in the coronary network for stimulation. Such probes are used together with an "active implantable medical device," as such devices are defined by Jun. 20, 1990 directive 90/385/CEE of the Council of the European Communities, and include, for example, a device such as a cardiac pacemaker, a defibrillator and/or a cardiovertor, and in particular, a pacemaker of the "multisite" type.

BACKGROUND OF THE INVENTION

Stimulation of the right heart cavities is typically achieved by implanting endocardial probes by the right peripheral venous network. However, in order to stimulate the left heart cavities, one typically introduces the endocardial probe into the coronary network. For example, for an electrode laid out vis-à-vis the left ventricle, the access to the entry of the coronary sinus is done via the right atrium.

The installation of such a probe is a particularly delicate intervention, because the position of the points of stimulation is very important. Thus, in the case of a pacemaker of the "multisite" type, the left ventricle and the right ventricle points of stimulation must be as distant from one another as possible to optimize the resynchronization of the whole of the cardiac cavities. In the same way, the stimulation of the left atrium imposes a very precise positioning of the probe in the network of the coronary veins. Of course, when the selected site is reached, the maintenance of the probe in the selected position must be ensured for the long and short term, regardless of the size of the vein.

The published EP-A-0 993 840 and its counterpart U.S. Pat. No. 6,385,492 B1 (commonly assigned herewith to ELA Médical) describe a coronary probe that is equipped with various elastic structures likely to provide a retention function, for example, by means of a ball at the distal end, eventually inflatable, of a chain of spheres of increasing diameters, of an elastic skirt, etc. These various retention structures, although effective to ensure the desired retention in place, nevertheless have a relatively complex structure that makes their construction and implementation difficult. Furthermore, those retention structures are rather adapted to sectoral electrode probes, being conceived to ensure an elastic pressure between the probe and the internal wall of the vein on the side opposed to that of the sectoral electrode, so as to accentuate the pressure of the sectoral electrode against the wall of the vein. Moreover, these retention structures can make the probe difficult to extract or to reposition, except when also envisaging a relatively complex structure able to ensure the reversibility of the implantation, for example, by implementing deflatable balls or turned up barbs.

Indeed, once the probe is installed, it is desirable to be able to extract it or to reposition it without damaging the veins of the coronary network. This imposes a need for a retention system that is not very traumatic in its configuration. In the same way, at the time of the implantation, more specifically at the time of the progression of the probe, the surgeon must be able to cross, without too many difficulties, the obstacles such as valvules or junctions of the coronary network. The retention structure therefore, must not interfere significantly, if at all, with these operations.

Lastly, it is recognized that the retention structure be conceived to allow the introduction of a probe into the internal lumen of reduced diameter of a guiding-catheter as well as the use of an axial stylet along which one can slide the probe (the latter being a probe installation technique known as "wire-guided").

OBJECTS AND SUMMARY OF THE INVENTION

It is, therefore, an object of the present invention is to propose a retention structure for a coronary probe that mitigates the various disadvantages mentioned above, and which in particular is:

1. of a form as less traumatic as possible,
2. compatible with the use of a sectoral probe or not,
3. compatible with the introduction into a catheter-guide of small diameter and the threading on an axial stylet, and
4. of entirely reversible implantation, so as to allow an extraction of the probe without damage of the vein.

It is a further object of the invention to propose a probe that, for any given size (size being limited only by the internal diameter of the lumen of the guiding-catheter used for installation of the probe) presents a maximum retention capacity, so that the surgeon can be assured that the electrode implanted will be maintained in position on the chosen site of stimulation, in a precise and durable way.

Broadly, the present invention is directed to a coronary probe of the general type described in EP-A-0 993 840 and U.S. Pat. No. 6,385,492 B1 above mentioned, i.e.; including a flexible hollow sheath comprising an internal electrical conductor; at the distal extremity of the sheath, an intermediate element with a cylindrical body carrying a retention structure; and an end forming a probe-head, having a protuberance at the distal extremity of the intermediate element and equipped with at least one stimulation electrode that is electrically conducting, connected to the internal conductor, and able to come in contact with an internal wall of the vein.

In a characteristic manner of the present invention, the retention structure includes at least one relief formed on the cylindrical body and presenting, as viewed from an end, an overall circular contour, so as to have locally a diameter that is increased as compared to the diameter of the cylindrical body.

Preferably, and advantageously, the overall circular contour is an eccentric contour having an axis that, compared to the axis of the cylindrical body, is offset, for example, offset a distance between the respective axes that is in a range of from between 15 and 25% of the diameter of the cylindrical body. In one embodiment, the diameter of the overall circular contour is preferably included between 1.5 and 2 times the diameter of the cylindrical body.

In a first embodiment, the retention structure of the probe relief includes a plurality of annular reliefs.

In a second and more preferred embodiment, the retention structure of the probe relief includes a helicoid relief having a thread extending around the cylindrical body. The thread can in particular include one or more of the following attributes:

1. be extended in a nonjointed manner around the cylindrical body, i.e., with a spacing between the threads as exists in a screw;
2. be extended around the cylindrical body for a number of turns, for example, two to three turns;

3. present a nominal thread radius that is variable along the length of the helix, more particularly, a radius that, moving from one end of the helix to the other, increases to a maximum radius, and then decreases, the maximum preferably occurring midway between the ends and variable radius being generally symetrical about the midway point;

4. present a maximum thread radius to be a value selected in the range of between 0.75 and 1 times the diameter of the cylindrical body;

5. present a thread having a constant pitch; and 6. be of a round profile.

BRIEF DESCRIPTION OF THE DRAWINGS

Other features, characteristics, and advantages of the present invention will appear to a person of ordinary skill in the art, in view of the following detailed description, made with reference to the annexed drawings, in which like reference characters refer to like elements, and in which:

FIG. 1 is an elevated perspective view of a probe according to a preferred embodiment of the present invention;

FIG. 2 is a view taken along lines II-II of FIG. 3; and

FIG. 3 is an end view taken along lines III-III of FIG. 2.

DETAILED DESCRIPTION OF THE INVENTION

With reference to the figures, reference 10 indicates the flexible sheath (in phantom lines) of the probe, of which only the distal end, which carries the probe-head is illustrated. This sheath 10 is hollow, so as to be able to thread it on an axial stylet used for guiding, and it carries an internal conductor that is connected, at the distal end, with an electrode of the probe and, at the proximal end, with a connector to the electric circuits of the active implantable medical device implanted in the body of the patient for delivery of stimulation pulses to, and for the sensing of electrical activity of, the patient.

Sheath 10 is assembled at its distal end to an intermediate element 12, characteristic of the invention and which will be described more in detail thereafter. Element 12, in turn, is assembled at its distal extremity to a probe-head 14 at the free end of the probe.

Probe-head 14 comprises, in the illustrated example, a cylindrical body 16 bearing at its free end an electrode in the shape of collar 20 made of a conducting material (for example, a microporous carbon), laid out along the diameter of body 16, and spaced a distance from the distal extremity of body 16. Probe head 14 also is equipped with a roughly hemispherical extremity structure 18 made of a silicone elastomer containing a steroid. Structure 18 provides for a progressive release of the steroid, making it possible to minimize an inflammatory reaction locally, and to reduce any rise in the stimulation voltage threshold, in the first weeks following the implantation of the lead. The silicone charged with the steroid additionally presents the advantageous property to increase its volume by absorption. One suitable lead for implementing the invention are leads of 'Situs' type sold by Ela Medical Montrouge, France. See also, U.S. Pat. No. 6,385,492 B1, the disclosure of which is incorporated herein by reference in its entirety.

Probe-head 14, similar to sheath 10 and intermediate element 12, is hollow to allow the threading of an axial stylet through an axial opening 22 of probe-head 14. Opening 22 is normally closed by a joint but can be penetrated in a tight fit by a stylet of the angioplasty type (not shown) allowing for a "wire guiding" of the probe. This angioplasty stylet can be, for example, the model 595-J-014 type manufactured by Cordis Corporation. It is a very fine stylet comprising a metal core covered by a spring and having a flexible extremity that can be introduced directly into the vessels without risk of perforation. This stylet, introduced into the central cavity of the probe 10, penetrates the sealed opening 22 and then progresses through the coronary network in order to select more easily a collateral vein. Once the vein is selected, the surgeon can slide the body of probe along the stylet, whose role will be that of a simple guide of small diameter axially guiding the body of probe into the coronary network.

One now will describe more in detail the structure of intermediate element 12, which carries the retention structure of the extremity of probe in the vein.

The retention structure is designed to function in a way that is to be able to exert a light pressure on the vein in order to establish a sure electrode contact independent of the cardiac movements, while maintaining in place there the probe-head, so as to minimize, if not eliminate, any risk from fluctuation inside the vein and any withdrawal or inopportune movement of the probe.

Element 12 is formed, on the major part of its length, of a cylindrical body 24, having the same diameter as sheath 10. It is connected to the probe-head 14, typically having a smaller diameter, by a truncated transition part 26. In one embodiment, the diameter of cylindrical body 24 and sheath 10 is, for example, 1.6 mm, and the diameter of the probe-head 14 is, for example, 1.3 mm (these dimensions, of course, being understood as not restrictive at all and being given only as an example). Truncated transition part 26 is thus illustrated as a conical section that matches at it ends, and connects, the different diameters.

In a characteristic manner of the invention, cylindrical body 24 carries on it a relief. In a preferred embodiment, the relief is the relief is in the shape of helicoid thread 28. Thread 28 presents a rounded profile, nontraumatic for the vein with which it will be in contact, and preferably extends at constant pitch over a limited number of turns of helix, for example, over 2½ turns as illustrated on the drawings. The turns are preferably nonjointed so as to provide between two turns of the thread an interval 30 whose width corresponds roughly to half of the width of thread 28.

Advantageously, thread 28 has a variable radius along its turns, initially growing in size from R1 to R2 until reaching a maximum value R3, and then decreasing in size R4, and then R5. In this way, the variable radius presents, from one extremity of the thread to the other, a progressive transition with the central area forming the most marked or maximum projection. See FIG. 2. The cylindrical body 24 by comparison has a radius of R0.

Moreover, and in a particularly advantageous manner, thread 28 has an axis A that is eccentric compared to the axis D of the cylindrical body 24 (see FIGS. 2 and 3) by an offset. This offset, indicated by distance x, is typically a value selected from between 15 and 25% of the diameter of the cylindrical body 24, for example, an offset of 0.3 mm for a diameter 2×R0=1.6 mm.

As illustrated from the extremity (FIG. 3), thread 28 presents a circular contour and the maximum radius R3 of thread 28 is selected according to the diameter of the internal lumen of the catheter-guide (not shown, but conventional in the art) with which the probe will be used so as to occupy to the maximum internal space of the lumen without friction. The high limit of radius R3 of the thread is, for example, selected so that overall circular contour has a maximal limit of size R2+R3=2.4 mm, this dimension being compatible with a catheter-guide of gauge 9 French (1 French=0.33 mm) having an internal diameter of 2.45 mm.

The offsetting of thread 28 compared to the axis of the probe makes it possible to increase to the maximum the height of thread 28 compared to the cylindrical body 24. This structure improves the quality of screwing the probe in the vein, increasing the retention force of the probe to a maximum. The material of the intermediate element 12, provided with a solid thread 28 formed by molding on the cylindrical body 24, is advantageously a silicone elastomer. Such a material is not very traumatic and has a good biocompatibility.

The presence of thread 28 offers a significant advantage with regard to the installation procedure. In this regard, at the time of implantation, once the probe has arrived at a stop in its displacement in translation in the vein, the surgeon can impose an additional movement of rotation to the body of probe. This makes possible, by effect of the screwing, a continued progression of the probe by a few millimeters into the vein, with a correlative reinforcement of the anchoring in the vein. If necessary, to increase the couple of screwing during this operation, it is possible to introduce into the body of probe a stylet equipped with a flat part rotating directly the extremity of the probe (e.g., as a screwdriver operates a complementary shaped head screw).

In an alternative embodiment, in the place of a thread extending for a plurality of helix turns, one can envisage a series of annular reliefs of eccentric axes compared to the axis of the cylindrical body, so as to obtain a higher retention-holding capacity for the same size.

One skilled in the art will appreciate that the present invention can be practiced by other than the described embodiments, which are presented for the purposes of illustration and not of limitation.

We claim:

1. A coronary probe for implantation in a vein of the coronary network for the stimulation of a left cavity of the heart, comprising:
    a flexible hollow sheath having an internal conductor and a distal end;
    an intermediate element, positioned at the distal end of the sheath, having a cylindrical body bearing a retention structure and a distal end wherein said cylindrical body further comprises a first diameter and a first axis at the median of the first diameter;
    a probe-head, positioned at the distal end of the intermediate element, having a protuberance and at least one stimulation electrode that is electrically conducting and connected to said internal conductor, said stimulation electrode being positioned on said probe-head to come in contact with said vein;
wherein said retention structure further comprises:
    at least one relief formed on the cylindrical body, said relief having an overall helicoid contour and a continuous ridge of variable radius extending around and for a length along the cylindrical body, said helicoid contour having a second diameter at the point where said variable radius is at a maximum, wherein said second diameter is greater than said first diameter;
    a second axis formed at the median of the second diameter that is offset from, and parallel to, the first axis;
wherein said overall helicoid contour further comprises an eccentric contour, relative to the first axis of the cylindrical body, that is centered on the second axis at the point where the variable radius is at a maximum.

2. The probe of claim 1, wherein the second axis is offset from said first axis by a distance x, with x being selected from between 15 and 25% of the first diameter of the cylindrical body.

3. The probe of claim 1, wherein the second diameter of the overall helicoid contour is comprised of between 1.5 and 2 times the first diameter of the cylindrical body.

4. The probe of claim 1, wherein the ridge extends in a nonjointed way around the cylindrical body.

5. The probe of claim 1, wherein the ridge extends around the cylindrical body over a number turns selected from between two to three turns.

6. The probe of claim 1, wherein the relief having an overall helicoid contour further comprises a first end and a second end and a nominal radius of the ridge, said nominal radius being a variable radius that increases and then decreases between said first and second ends. pg,15

7. The probe of claim 1, wherein the relief having an overall helicoid contour further comprises the ridge having a constant distance between the ridge turns.

8. The probe of claim 1, wherein the ridge further comprises a ridge having a round profile.

* * * * *